United States Patent [19]

Powell

[11] 4,044,612
[45] Aug. 30, 1977

[54] PROBE FOR OBTAINING GAS SAMPLES FROM A SHAFT FURNACE

[75] Inventor: Russell A. Powell, Pittsburgh, Pa.

[73] Assignee: Koppers Company, Inc., Pittsburgh, Pa.

[21] Appl. No.: 759,430

[22] Filed: Jan. 14, 1977

[51] Int. Cl.² .............................................. G01N 1/26
[52] U.S. Cl. .................................. 73/341; 73/421.5 R
[58] Field of Search .......................... 73/421.5 A, 341

[56] References Cited

U.S. PATENT DOCUMENTS

| 3,130,584 | 4/1964 | Kennedy | 73/421.5 A |
| 3,240,069 | 3/1966 | Kennedy | 73/421.5 A |
| 3,888,123 | 6/1975 | Kuntziger et al. | 73/421.5 A |

Primary Examiner—S. Clement Swisher
Attorney, Agent, or Firm—R. Lawrence Sahr; Oscar B. Brumback

[57] ABSTRACT

An elongate probe to obtain gas samples and temperature readings at selected locations in the burden of a furnace such as a blast furnace includes: an outer shell; an axially arranged inner shell; spaced apart baffles in the inner shell forming gas sample chambers; conduits communicating each with a respective chamber; sheathed thermocouples, each having a sensing end, arranged in a respective chamber; each sheathed thermocouple leading out of the inner shell; and means for flowing cooling fluid in the annulus between the inner and outer shells.

10 Claims, 8 Drawing Figures

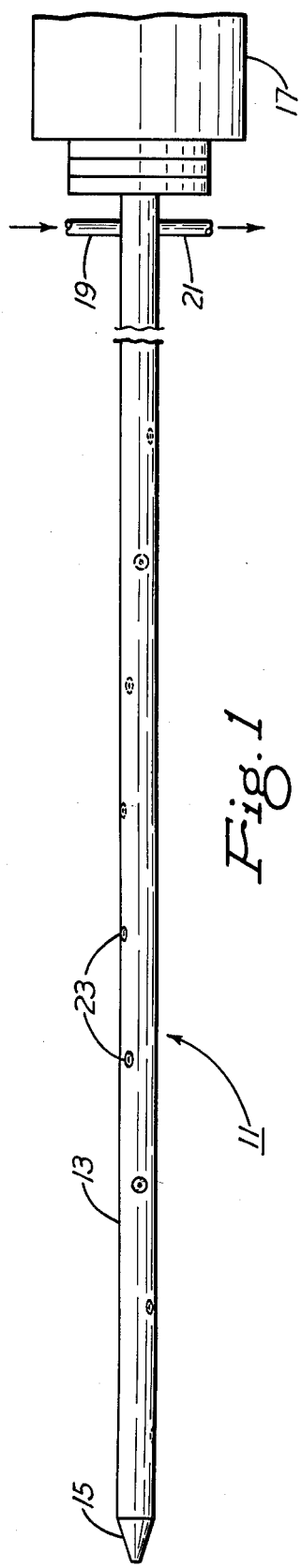
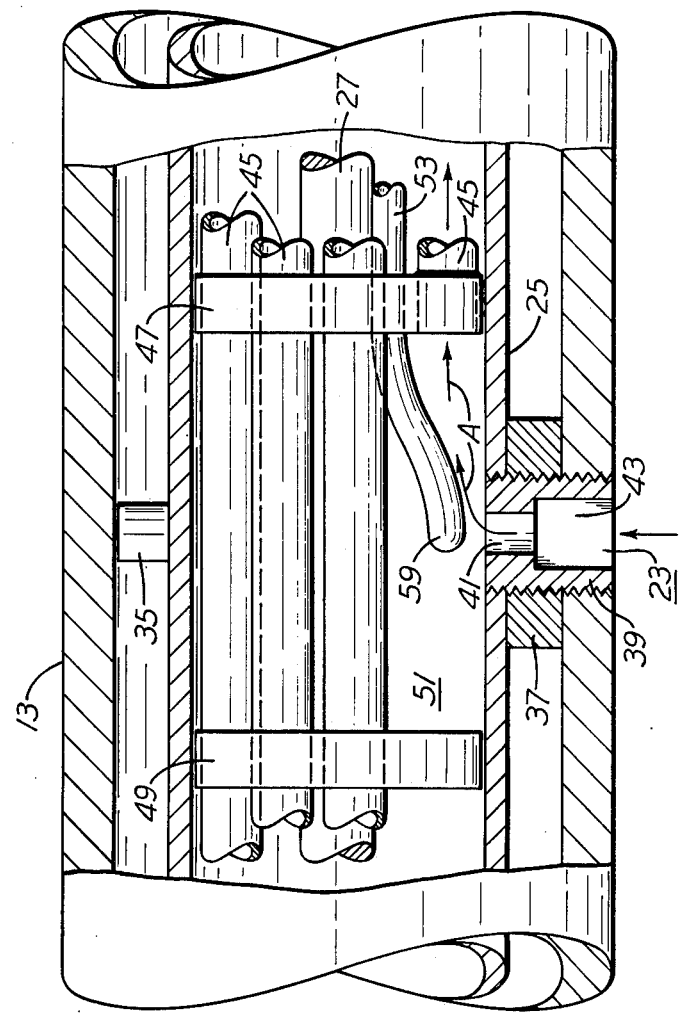

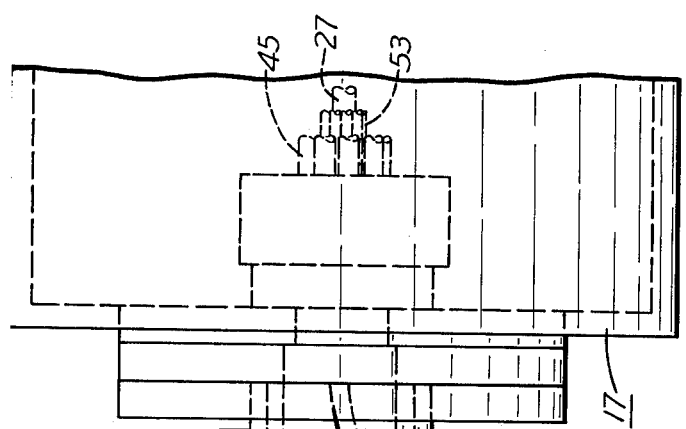

PROBE FOR OBTAINING GAS SAMPLES FROM A SHAFT FURNACE

BACKGROUND OF THE INVENTION

1. Field of the Invention

The present invention is related to shaft furnaces and, more particularly, to a probe for use in obtaining gas samples from within a shaft furnace during operation such as a blast furnace.

2. Description of the Prior Art

The present invention is an improvement in apparatus for taking gas samples in shaft furnaces, particularly blast furnaces, as shown and described in U.S. Pat. No. 3,888,123. This patent also refers specifically to U.S. Pat. No. 3,240,069 as one other embodiment of a blast furnace probe.

U.S. Pat. No. 3,888,123 discloses an elongate cylindrical tube comprised of an outer tube and a concentric inner tube. The outer tube is perforated at selected locations by ports leading to gas tubes arranged lengthwise of the outer tube, but within the annulus between the inner and outer tubes. In each gas tube there is a thermocouple that is located at the perforation in the outer tube; each thermocouple being connected by a suitable signal conductor to an indicator. The probe is moved into and out of the furnace by means of a motor, and a vibrator is also provided to assist in moving the probe into the furnace.

How the present invention differs from the probe shown and described in U.S. Pat. No. 3,888,123 will become clear after reading the following detailed description of an embodiment of the present invention.

U.S. Pat. No. 3,240,069, referred to previously herein, also shows and describes a blast furnace probe that comprises an outer tube that is made up of cylindrical sections of varying diameters and tubular reducers. Thus, the tubular probe has a small diameter at the end entering the furnace and a relatively large diameter at the end outside the furnace wall, with stepped increasing diameter between the ends. A plurality of thermocouples are spaced along the length of the probe, and they are encased in tubular projections from the main stepped diameter tube. Associated with each tubular projection and the thermocouple, are gas ports in the projecting tubes through which gas samples enter a gas conduit leading to each projecting tube.

How the present invention differs from the blast furnace probe of U.S. Pat. No. 3,240,069 will become evident after reading the following detailed description of one embodiment of the present invention.

SUMMARY OF THE INVENTION

Apparatus adapted to take gas samples and to measure the temperature of the ambient at selected radial locations at a level in a shaft furnace comprises inner and outer coaxial tubes with the outer tube having one shaped end adapted to penetrate the burden. An axial rod is disposed within the inner tube and spaced-apart, annular baffles surround the axial rod in spaced apart relation within the inner tube, forming a plurality of gas sampling chambers. Gas entry ports in the inner and outer tubes communicate with respective chambers and are arranged helically in said tubes. Gas sample conduits are disposed in the inner tube and around the axial rod, each conduit terminating in a respective chamber. Sheathed thermocouples surround the axial rod and each thermocouple terminates in a sensing end in a respective chamber. Insulating material surrounds the axial rod and the sheathed thermocouples where they pass through each baffle. A driving yoke is connected to the apparatus at the end opposite the shaped end.

For a further understanding of the invention and for features and advantages thereof, reference may be made to the following description and the drawings which illustrate a preferred embodiment of equipment in accordance with the invention.

BRIEF DESCRIPTION OF THE DRAWINGS

In the drawings:

FIG. 1 is a schematic view of a probe in accordance with one embodiment of the invention;

FIG. 2 is a schematic view of the probe of FIG. 1 showing it at a larger scale;

FIG. 6 is a typical cross-sectional view taken on line VI-VI of FIG. 2;

FIG. 7 is a longitudinal sectional view at one end of the probe of FIG. 1, partly in section.

DETAILED DESCRIPTION

Figure 5:
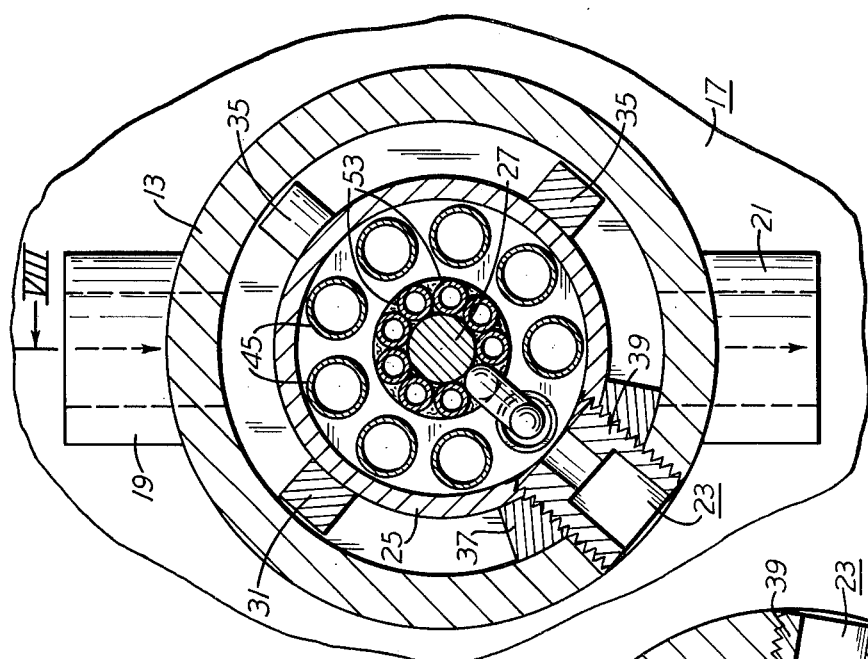
FIG. 5 is a view along line V—V of FIG. 2.

Referring to FIG. 1, a probe 11 for use in a shaft furnace, such as a blast furnace, includes an elongate cylindrical tubular shell 13 having one tapered end portion 15 and a drive yoke 17 at the other end. The shell 13 is provided with an inlet 19 and an outlet 21 tubular conduit for cooling water. Also, the shell 13 is provided with a plurality of gas inlet ports 23 that are regularly and helically arranged around the shell 13.

As shown in FIG. 5, concentrically arranged within the outer tubular shell 13 is an inner tubular shell 25, and within the inner tubular shell 25, there is a solid rod 27 disposed axially of both tubular shells 13 and 25.

Referring to FIG. 2, it will be noted that the inner tubular shell 25 has a rounded cap 29 at the end near the tapered end portion 15, and that the outer surface of the inner tubular shell 25 supports and carries two helically and regularly arranged baffles 31, 33.

Figure 4:
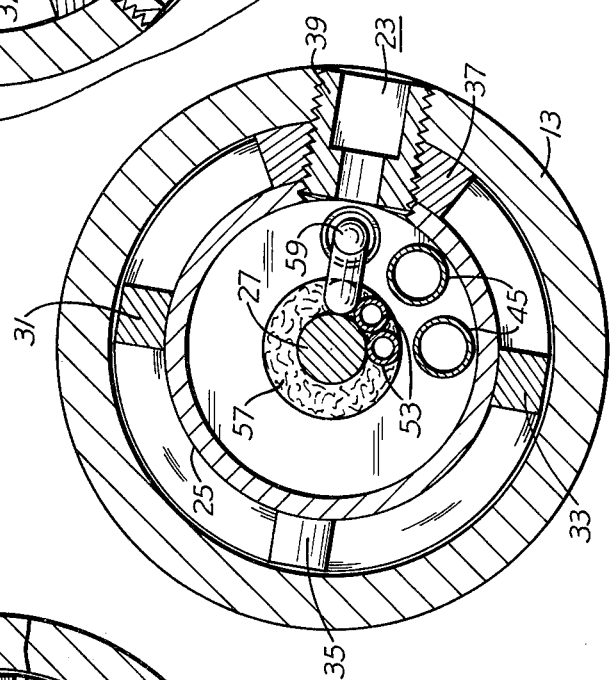
FIG. 4 is a view along line IV—IV of FIG. 2.
Figure 3:
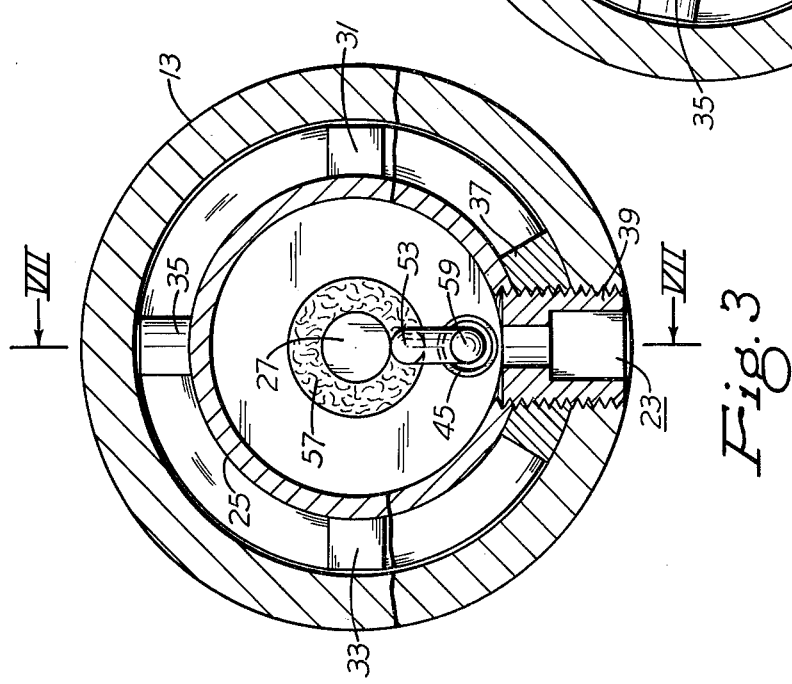
FIG. 3 is a view along line III—III of FIG. 2.

At convenient locations on the inner shell 25, there are fitted spacer pieces 35 that may be cut from solid rod material if desired. The spacer pieces 35 cooperate with the inner surface of the outer shell 13 during the assembly of the gas inlet ports 23. The spacer pieces 35 are located most conveniently opposite the gas inlet ports 23, as shown in FIGS. 3-5.

As shown in FIGS. 3-7, each gas inlet port 23 includes an arcuate spacer piece 37 that is fixed to the inner tubular shell 25 and cooperates with the inner surface of the outer tubular shell 13. Threaded into the inner tubular shell 25 and into the spacer piece 37 and the outer tubular shell 13 is a plug 39 having a cylindrical bore 41 therein and a reentrant socket 43, for a conventional hexagonal wrench, as for set screws.

Referring to FIG. 5, it will be noted that the inner tubular shell 25 surrounds a plurality, nine being shown as an example, of tubular members 45, each tubular member 45 is a gas collecting tubular conduit.

Referring to FIG. 6, which illustrates a typical longitudinal section of the probe 11, it will be seen that a typical gas collecting tubular conduit 45 is welded into and terminates in an annular baffle plate 47 disposed transversely in the inner tubular shell 25. Spaced apart longitudinally from the annular baffle 47 is another annular baffle plate 49, in which, though not shown, terminates another gas collector tubular conduit 45.

The space between the annular baffles 47, 49 constitutes a small gas sampling compartment 51 into which gases flow through the gas inlet port 23. Thus, adjacent spaced-apart, annular baffles 47, 49, throughout the length of the probe 11, create a plurality of respective small gas sampling compartments.

Referring to FIG. 5, it will be observed that there are a number — nine being shown typically — of sheathed thermocouples 53 disposed around the solid axial rod 27. At each annular baffle 47, 49 only, the space 55 between the sheathed thermocouples 53 is suitably packed with an insulating material, such as ceramic wool.

In FIG. 6, then, a typical one of the sheathed thermocouples 53, with a suitable sensing end 59, is bent downward and terminates in the typical gas sampling compartment 51; the sensing end 59 itself being located close to the hole 41 in the plug 39.

FIG. 6 also illustrates the flow of gases, designated by arrows A, from the furnace into the gas sampling compartment 51 and thence into the gas collecting tubular couduit 45.

Referring to FIG. 7, it will be seen that an end gas collecting compartment 51a is created between the annular baffle plate 49 and the rounded closed end of the inner tubular shell 25. The thermocouple 59 is shown positioned at the gas inlet hole 23 in the shell 13 and inner tubular shell 25.

FIG. 7, and FIG. 2 also, illustrates the terminus of the spirally arranged baffle 31 on the outside of the inner tubular shell 25, and in the annulus between the inner 25 and outer 13 shells. As shown by the arrows B, cooling water or other fluid courses around the terminus of the spirally arranged baffle 31 and is directed back toward the outlet water connection 21.

Figure 8:
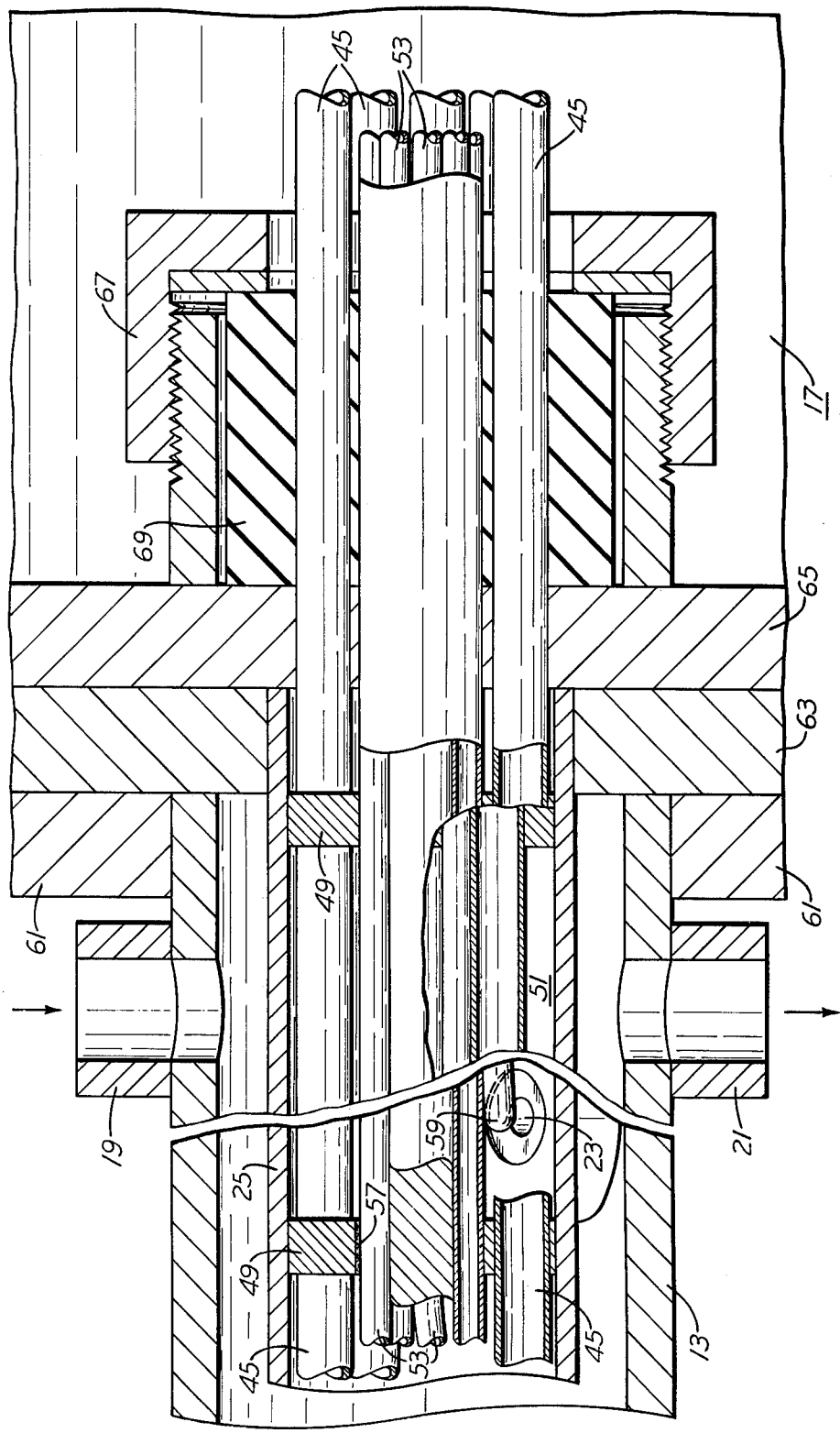
FIG. 8 is a longitudinal sectional view at the other end of the probe of FIG. 1, also partly in section.

Referring to FIG. 8, it will be noted that the outer tubular shell 13 terminates in a flange 61, and that the inner tubular shell 25 terminates in another flange 63 which is bolted to the flange 61, as in any conventional manner. The flange 63 abuts another flange-like plate 65 forming part of the drive yoke 17.

As shown in FIG. 8, the several gas tubular conduits 45 and the sheathed thermocouples 53 pass through properly sized openings in the flangelike plate 65 into the drive yoke 17. Surrounding the cables 53 and the gas conduits 45 is a stuffing box 67 which is packed with a suitable substance 69. One such substance which is satisfactory is known as Room Temperature Vulcanizing Silicone Rubber, that is manufactured and sold by the General Electric Company.

Those skilled in the art will appreciate that the several sheathed thermocouples 53, and the several gas sampling tubular conduits 45 are connected to suitable apparatus, not shown, for the purposes of recording temperatures measured by each thermocouple, and analyzing gas samples collected by each individual tube.

In operating a shaft furnace, like a blast furnace for example, it is desirable to obtain both gas samples and temperature values at several radial positions at a preselected level of said furnace. Such samples of gas have heretofore been obtained by inserted fixed probes. U.S. Pat. No. 3,888,123, mentioned previously herein, illustrates a probe that can be inserted into and withdrawn from a furnace. Such probe includes a plurality of apertures, like aperture 18, in an outer tubular shell. Coaxial with the outer tubular shell is an inner tubular member or supporting tube. A plurality of gas distribution pipes surround the central supporting tube and an aperture like 18 admits a gas sample to each gas distribution pipe. Cooling water flows in the interstices between the inner and outer tubular members and the gas distribution pipes to cool the probe and water flows through the coaxial central tubular member and thence out of the probe.

It is known that the apertures in the probe of the prior art become clogged with dust in the blast furnace gas when the apertures are partially obstructed by a thermocouple, and that the thermocouples may become thermally grounded and thereby inoperative.

In contrast to the probes of the prior art that have not proved to be satisfactory for taking temperatures and gas samples simultaneously for the reason stated herein, the present probe separates the sheathed thermocouples from the gas sampling tubes, so that obstruction of the gas flow and thermal grounding do not occur.

From the foregoing description of one embodiment of the invention, those skilled in the art should recognize many important features and advantages of it, among which the following are particularly significant:

That the sheathed thermocouples and sensing ends associated therewith are each spaced apart from and are not thermally grounded in any way;

That the gas passages in the present probe are clear and open to admit a gas sample into the probe unobstructedly;

That the entire assembly of sheathed thermocouples is easily and quickly removable from the tubular shell; wherefore, a replacement assembly may be quickly inserted into the tubular shell while the removed assembly is serviced as necessary.

Although the invention has been described herein with a certain degree of particularity, it is understood that the present disclosure has been made only as an example and that the scope of the invention is defined by what is hereinafter claimed.

What is claimed is:

1. Apparatus adapted to take samples of gas from a plurality of locations within the burden in a shaft furnace and to measure the ambient temperature in said furnace at said locations, comprising:
   a. a hollow tubular outer shell having one shaped closed end adapted for penetrating said burden;
   b. a hollow tubular inner shell having one closed end adjacent said closed end of said outer shell;
   c. means for maintaining said inner shell axially aligned within said outer shell and spaced apart therefrom;
   d. means within said inner tubular shell subdividing the interior thereof into a plurality of chambers;
   e. a plurality of gas entry ports in said outer and inner shells, each said port communicating with a respective chamber in said inner shell;
   f. an axial supporting member extending lengthwise within said tubular inner shell;
   g. a plurality of gas sampling conduits arranged around said axial supporting member in spaced relation thereto, each said gas sampling conduit communicating with a respective chamber in said inner shell;
   h. a plurality of sheathed thermocouples arranged around said axial supporting member and disposed between said gas sampling conduits and said axial supporting member, each sheathed thermocouple terminating in a sensing end disposed in a respective chamber in said inner shell; and
  i. means for flowing a cooling fluid in the annulus between said inner and outer shells.

2. The invention of claim 1 wherein:
  a. said gas entry ports are helically arranged in said elongate outer shell and inner shell.

3. The invention of claim 1 including:
  a. cooling fluid entry means in said outer shell;
  b. cooling fluid exit means in said outer shell; and
  c. means in the annulus between said inner and outer shells for guiding cooling fluid lengthwise and around the outer periphery of said inner shell from said fluid entry means to said fluid exit means.

4. The invention of claim 3 wherein:
  a. said means in the annulus is at least two elongate baffles arranged helically around said outer periphery of said inner shell.

5. The invention of claim 1 wherein:
  a. said means subdividing the interior of said inner tubular shell includes a plurality of spaced apart annular baffles disposed around said axial supporting member and transversely to the axis of said inner shell.

6. The invention of claim 1 including:
  a. insulating means surrounding said axial supporting member and said sheathed thermocouples in way of each one of said annular baffles.

7. The invention of claim 1 including:
  a. a drive yoke connected to said apparatus at the end thereof opposite said shaped end.

8. Apparatus adapted to take samples of gas from a plurality of locations within the burden in a shaft furnace and to measure the ambient temperature in said furnace at said locations, comprising:
  a. a hollow tubular outer shell having one shaped closed end adapted for penetrating said burden;
  b. a hollow tubular inner shell having one closed end adjacent said shaped closed end of said outer shell;
  c. spacers disposed oppositely in the annulus between said inner and outer shells that maintain said shells coaxial;
  d. an axial supporting member extending lengthwise within said tubular inner shell;
  e. a plurality of spaced apart annylar baffles disposed transversely within said tubular inner shell and around said axial supporting member in spaced apart relation thereof, thereby forming a plurality of gas receptive chambers within said inner shell;
  f. a plurality of gas entry ports in said outer and inner shells communicating each with a respective chamber;
  g. a plurality of gas sampling tubular conduits within said inner shell supported by said baffles and disposed around said axial supporting member, a gas sampling tubular conduit terminating at each chamber;
  h. a plurality of sheathed thermocouples arranged around said axial supporting member, each said cable terminating in a thermocouple element disposed in a respective chamber;
  i. at least two helically arranged baffles mounted to the outer surface of said inner shell and disposed within the annulus between said inner and outer shells;
  j. means for flowing cooling fluid into said annulus and means for flowing said cooling fluid out of said annulus; and
  k. drive yoke means connected to said apparatus at the end thereof opposite said shaped end.

9. The invention of claim 8 wherein:
  a. said gas entry ports are disposed helically in said outer and inner shells.

10. The invention of claim 8 including:
  a. insulating means disposed around said axial supporting member and said sheathed thermocouple where said cables pass through said baffles.

* * * * *